United States Patent [19]

Peters et al.

[11] Patent Number: 5,892,047
[45] Date of Patent: Apr. 6, 1999

[54] PROCESS FOR THE PREPARATION OF SUBSTITUTED 4-ETHYL-PIPERIDINES AND AN INTERMEDIATE FOR THE PREPARATION OF SAME

[75] Inventors: Dan Peters; Oskar Axelsson, both of Malmö, Sweden

[73] Assignee: NeuroSearch A/S, Glostrup, Denmark

[21] Appl. No.: 849,852

[22] PCT Filed: Dec. 15, 1995

[86] PCT No.: PCT/EP95/04975

§ 371 Date: Sep. 4, 1997

§ 102(e) Date: Sep. 4, 1997

[87] PCT Pub. No.: WO96/19452

PCT Pub. Date: Jun. 27, 1996

[30] Foreign Application Priority Data

Dec. 21, 1994 [DK] Denmark .................................. 1455/94

[51] Int. Cl.[6] ........................ C07D 211/14; C07D 211/46; C07D 401/12; A61K 31/445

[52] U.S. Cl. ......................... 546/236; 546/133; 514/305; 514/317

[58] Field of Search ..................... 514/305, 317; 546/133, 236

[56] References Cited

FOREIGN PATENT DOCUMENTS

| | | |
|---|---|---|
| 92/02502A1 | 2/1992 | WIPO . |
| 93/15052A1 | 8/1993 | WIPO . |

OTHER PUBLICATIONS

Axelsson, O. et al, J. Heterocyclic Chem. 1997, 34, pp. 461–463.
Ibata et al., Chem. Lett., (6) 1187–90 (1987).
Axelsson et al., Org. Prep. Proced. Int., 27(5), 571–2 (Oct. 1995).
Lu et al., Macromolecules, 25(18), 4464–8 (1992).
Pietra et al., J. Chem. Soc. D, (5), 297–8 (1970).
Schmidt et al., Chem.–Ztg., 109(10) 333–9 (1985).
Kornblum et al., J. Org. Chem., 53(7), 1475–81 (1988).
Jung et al., J. Org. Chem., 50(25), 5440–1 (1985).
Lindborg et al., Acta Pharm. Suec., 21(5), 271–94 (1984).
Harris et al., Stud. Surf. Sci. Catal., 84 (Zeolites and Related Microporous, Pt. A.), 29–36 (1994).
Bacaloglu et al., Langmuir, 7(6), 1107–11 (1991).
Patent Abstracts of Japan, vol. 14, No. 359 (E–959) [4302] Aug. 3, 1990.
Sundermeyer et al., Chem. Ber., 123(8), 1687–90 (1990).
Imamura et al., Bull. Chem. Soc. Jpn, 60(10), 3499–504 (1987).
Gupta et al., Arch. Pharm, vol. 317, 1010–1017 (1984).
Bagli et al., J. Med. Chem., vol. 27, No. 7, 875–881 (1984).

*Primary Examiner*—Alan L. Rotman
*Attorney, Agent, or Firm*—Birch, Stewart, Kolasch & Birch, LLP

[57] ABSTRACT

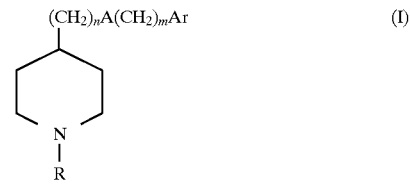

Compounds of structure (I) in which R is $C_{1-8}$alkyl(phenyl)p, $C_{2-8}$alkenyl(phenyl)p, $C_{2-8}$ alkenyl(phenyl)p, $C_{3-8}$cycloalkyl or $C_{1-8}$alkyl$C_{3-8}$cycloalkyl; p is 0 to 2; n is 0 to 6; A is a bond, oxygen, sulphur or $NR^1$; $R^1$ is hydrogen, $C_{1-8}$alkylphenyl$C_{1-4}$alkyl; m is 0 to 3; and Ar is aryl or heteroaryl, each of which may be optionally substituted, and salts thereof processes for preparing said compounds, pharmaceutical compositions containing them and their use in therapy, in particular as calcium blocking agents.

4 Claims, No Drawings

PROCESS FOR THE PREPARATION OF SUBSTITUTED 4-ETHYL-PIPERIDINES AND AN INTERMEDIATE FOR THE PREPARATION OF SAME

FIELD OF INVENTION

The present invention relates to a novel process for the preparation of substituted 4-ethyl-piperidines and intermediates for the preparation of same. The substituted 4-ethyl-piperidines prepared according to the invention are useful in therapy as calcium channel blocking agents.

BACKGROUND OF INVENTION AND PRIOR ART

The substituted 4-ethyl-piperidines prepared according to the invention and their activity as calcium channel blocking agents are disclosed in WO-A1-92/02502, WO-A1-93/15052, and Neuropharmacology, Vol. 32, No. 11, p. 1249–1257 (1993). These publications describes several methods for the preparation of the compounds, using piperidines or pyridines as starting materials. It has now been found that substituted 4-ethyl-piperidines can be prepared by a very convenient, high yielding, one pot, two step synthesis, from readily available starting materials.

OBJECTS OF THE INVENTION

It is the object of the present invention to provide a novel method for the preparation of substituted 4-ethyl-piperidines, which is convenient and high yielding, using readily available starting materials. Furthermore, it is an object of the present invention to provide novel intermediates useful for the preparation of substituted 4-ethyl-piperidines.

SUMMARY OF THE INVENTION

In detail the invention, then, comprises inter alia the following:

A process for the preparation of substituted 4-ethyl-piperidines having the formula

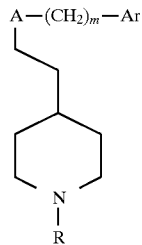

or a salt thereof
wherein
R is $(aryl)_p akyl$, $(aryl)_p alkenyl$ or $(aryl)_p alkynyl$, wherein the aryl groups may be substituted; cycloalkyl; or cycloalkylalkyl;
p is 0, 1 or 2;
m is 0, 1, 2, 3, 4, 5 or 6;
A is O, S or $NR^1$, wherein $R^1$ is hydrogen, alkyl or phenylalkyl;
and Ar is aryl or heteroaryl, each of which may be substituted; which comprises the step of reacting a quinuclidinium salt of formula

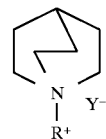

wherein R is as defined above and Y is a counter ion, with a compound of the formula $HA-(CH_2)_m-Ar$ or a reactive derivative thereof, and thereafter optionally forming a salt thereof;
a process as above, wherein A is O;
a process as above, wherein m is 0 and Ar is 3, 4-dichlorophenyl;
a process as above, wherein R is pentyl;
a process as above, wherein the reaction takes place in the presence of a base;
a process as above, wherein the base is an inorganic base;
a process as above, wherein the base is $Cs_2CO_3$;
a compound of the formula

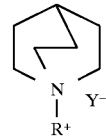

wherein R and Y is as defined a bove; provided that when R is alkyl, the alkyl group contains at least three carbon atoms, and Y is not bromide; and
the use of a compound of the formula

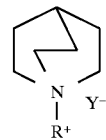

wherein R and Y are as defined above, as an intermediate in the preparation of substituted 4-ethyl-piperidines.

To the above formulas the following applies:

Alkyl means a straight or branched chain of from one to eight carbon atoms, including but not limited to, methyl, ethyl, propyl, isopropyl, butyl, sec-butyl, tert-butyl, pentyl, hexyl, and heptyl.

Alkenyl and alkynyl means straight or branched chains of from two to eight carbon atoms, with respectively, at least one double dr triple bond, and including but not limited to ethenyl, 1,2- or 2,3 propenyl, 1,2- or 3,4-butenyl, ethynyl, 2,3-propynyl, 2,3- or 3,4-butynyl.

Cycloalkyl means cyclic alkyl of from three to eight carbon atoms, including but not limited to cyclopropyl, cyclobutyl, cyclopentyl, cyclohexyl and cycloheptyl. Cycloalkylalkyl is cycloalkyl and alkyl as above.

It is to be understood that the $(aryl)_p akyl$, $(aryl)_p alkenyl$ and $(aryl)_p alkynyl$ and cycloalkylalkyl groups R, are linked to the piperidine nitrogen atom via the alkyl, alkenyl and alkynyl moieties respectively.

Suitable aryl groups include, for example, unsaturated, partially saturated or saturated monocyclic, bicyclic or tricyclic ring systems of up to fifteen carbon atoms, such as, for example, phenyl, naphthyl, tetrahydronaphthyl, fluorene, flurenone, dibenzosuberene, and dibenzosuberenone.

Suitable heteroaryl groups include, for example, unsaturated, partially saturated, or saturated monocyclic, bicyclic or tricyclic ring systems of up to fifteen carbon atoms containing at least one heteroatom, such as pyridyl, thienyl, imidazolyl, quinolinyl, tetrahydroquinolinyl, benzofuranyl. A tricyclyclic ring system most preferably has the structure:

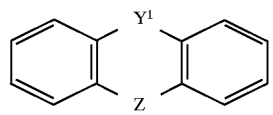

wherein $Y^1$ represents $-X(CH_2)_r-$, X is O, S, or NR (where R is hydrogen or $C_{1-4}$alkyl), Z is $-(CH_2)_q-$ or $-CH=CH-$, q is 0, 1 or 2 and r is 0 or 1 or is a corresponding dehydro ring system. Examples of tricyclic heteroaryl groups include dibenzofuranyl, dibenzothienyl, carbazole, N-methylcarbazole, acridine and dibenzooxepine. The heteroaryl ring can be linked to the remainder of formula via any suitable ring atom.

Suitable substituents on the aryl and heteroaryl rings includes, for example, 1–3 substituents selected from halogen, nitro, CN, $CF_3$, $OCF_3$, alkyl, alkoxy, alkylthio, $NH_2$, NHalkyl, N(alkyl)$_2$, $C_{1-2}$alkylenedioxy, and optionally substituted phenyl, phenoxy, benzoyl, phenylalkyl (e.g. benzyl), or phenylalkoxy (e.g. benzyloxy).

Suitable substituents on said optionally substituted phenyl, phenoxy, benzoyl, phenylalkyl and phenylalkoxy include for example alkyl, alkoxy, halogen, $CF_3$ and nitro.

Examples of salts include pharmaceutically acceptable inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids, such as oxalic acid, may also be useful in the preparation of salts according to the invention.

THE INVENTION

As already stated the invention provides a convenient, high yielding process for the preparation of substituted 4-ethyl-piperidines, using readily available starting materials. The following scheme illustrates the novel process of the invention, which is normally carried out as a one-pot reaction:

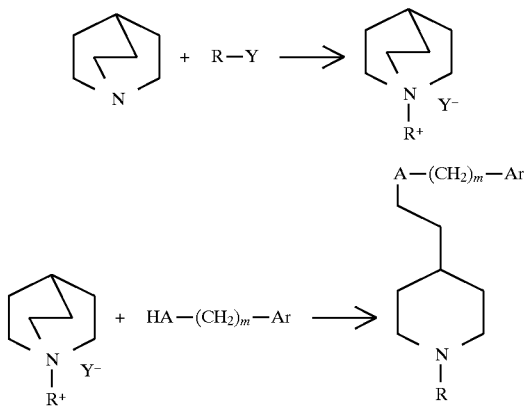

The quartemization of the quinuclidine ring may be carried out in conventional manner, without the use of solvent, or in an organic solvent, for example an alcohol, such as methanol, ethanol, isopropanol and phenol, an ether such as diisopropylether, tetrahydrofuran or dioxan, an amide such as dimethylformamide, or in a halogenated-, aromatic- or aliphatic hydrocarbon such as chloroform, dichlormethan, benzene, toluene, xylene and hexane. Preferably the reaction is carried out without the use of solvent.

The leaving group Y may be a halide, such as bromide, chloride or iodide or a sulfonyloxy group such as methylsulphonyloxy, benzenesulphonyloxy, or p-toluenesulphonyloxy Temperatures between 20° C. and 200° C. is appropriate for the reaction.

The ring opening reaction may be carried out without the use of solvent or in an inert solvent with high boiling point. Preferably the reaction is carried out without the use of solvent.

Preferably the ring opening reaction is carried out in the presence of an organic or inorganic base, for example hydroxides, such as NaOH, KOH, CsOH, or RbOH or carbonates, such as $Na_2CO_3$, $K_2CO_3$, $Cs_2CO_3$, $Rb_2CO_3$, $NaHCO_3$, $KHCO_3$, and $CsHCO_3$. Preferably the reaction takes place in the presence of $Cs_2CO_3$.

Temperatures between 100° C. and 250° C., preferably between 150° C. and 200° C., are appropriate for the reaction. Suitably the reaction is carried out in an inert atmosphere.

The products of the reactions described herein are isolated by conventional means such as extraction, crystallisation, distillation, chromatography and the like.

Starting materials for the processes described herein are known or can be prepared by known processes from commercially available chemicals.

DETAILED DESCRIPTION OF THE INVENTION

The invention will now be described in greater detail with reference to the following example, which are given by way of illustration only and are not to be construed as limiting.

EXAMPLE 1

4-[2-(3,4-dichlorophenoxy)ethyl]-1-pentylpiperidine, hydrochloride.

Quinuclidine (1.11 g, 10 mmol) was quartemized by heating with 1 -bromopentane (1.51 g, 10 mmol ) without solvent for one hour at 11 0° C. To this salt was then added 3,4-dichlorophenol (2.44 g, 15 mmol) and cesium carbonate (3.26 g, 10 mmol). The flask was flushed with nitrogen and the mixture was heated to 170° C. (bath temperature) for 15 hours. After cooling to room temperature, the crude product was dissolved in a mixture of ether (50 ml) and water (50 ml). The phases were separated and the aqueous layer was extracted once more with a 50 ml portion of ether. The combined organic phases were dried over magnesium sulphate. Pure 4-[2-(3,4-dichlorophenoxy)ethyl]-1-pentylpipendine, according to TLC ($CH_2Cl_2$/EtOH, 9:1), could then be precipitated as the hydrochloride by the addition of methanolic HCl (2.5 mL of a 4.3M solution). Yield: 3.0 g (7.9 mmol), 79% from quinuclidine. Mp 177°–178° C. (Lit. 177°–178° C.), The melting point rose to 178°–179° C. when the product was recrystallized from a mixture of methanol and ethyl acetate (1:1). The $^1H$ NMR spectrum at 500 MHz and the El mass spectrum of the product was in accordance with the structure.

We claim:

1. A process for the preparation of substituted 4-ethyl-piperidines having the formula

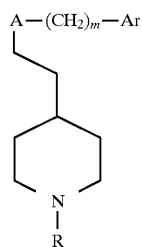

or a salt thereof
wherein
R is (aryl)$_p$alkyl, (aryl)$_p$alkenyl or (aryl)$_p$alkynyl, wherein the aryl groups are optionally substituted; cycloalkyl; or cycloalkylalkyl;
p is 0, 1 or 2;
m is 0, 1, 2, 3, 4, 5 or 6;
A is O, S or NR$^1$, wherein R$^1$ is hydrogen, alkyl or phenylalkyl; and Ar is aryl or heteroaryl, each of which are optionally substituted; which comprises the step of reacting a quinuclidinium salt of formula

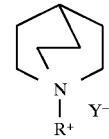

wherein R is as defined above and Y is a counter ion in the presence of Cs$_2$CO$_3$, with a compound of the formula HA-(CH$_2$)$_m$-Ar or a reactive derivative thereof, and thereafter optionally forming a salt thereof.

2. A process as in claim 1, wherein A is 0.
3. A process as in claim 1, wherein m is 0 and Ar is 3, 4-dichlorophenyl.
4. A process as in claim 1, wherein R is pentyl.

* * * * *